(12) United States Patent
Wood (10) Patent No.: US 11,325,102 B2
(45) Date of Patent: May 10, 2022

(54) PARTICULATE MATERIAL AND A METHOD FOR REMOVING ONE OR MORE CONTAMINANTS FROM HYDROCARBON GAS

(71) Applicant: COMMONWEALTH SCIENTIFIC AND INDUSTRIAL RESEARCH ORGANISATION, Acton (AU)

(72) Inventor: Colin Wood, Swanbourne (AU)

(73) Assignee: COMMONWEALTH SCIENTIFIC AND INDUSTRIAL RESEARCH ORGANISATION, Acton (AU)

( * ) Notice: Subject to any disclaimer, the term of this patent is extended or adjusted under 35 U.S.C. 154(b) by 197 days.

(21) Appl. No.: 16/463,457

(22) PCT Filed: Nov. 23, 2017

(86) PCT No.: PCT/AU2017/051294
§ 371 (c)(1),
(2) Date: May 23, 2019

(87) PCT Pub. No.: WO2018/094466
PCT Pub. Date: May 31, 2018

(65) Prior Publication Data
US 2019/0351390 A1 Nov. 21, 2019

(30) Foreign Application Priority Data
Nov. 25, 2016 (AU) ................................ 2016904850

(51) Int. Cl.
*B01J 20/26* (2006.01)
*B01D 53/02* (2006.01)
(Continued)

(52) U.S. Cl.
CPC ............ *B01J 20/267* (2013.01); *B01D 53/02* (2013.01); *B01D 53/1475* (2013.01);
(Continued)

(58) Field of Classification Search
CPC .... B01J 20/267; B01J 20/22; B01J 20/28004; B01J 20/28016; B01J 20/28047;
(Continued)

(56) References Cited

U.S. PATENT DOCUMENTS 8,057,576 B1 * 11/2011 Pollack .................... B01J 20/12
95/108

FOREIGN PATENT DOCUMENTS

| CA | 2769060 | 8/2013 |
| JP | 2012-179584 | 9/2012 |

(Continued)

OTHER PUBLICATIONS

International Search Report for PCT/AU2017/051294 dated Feb. 7, 2018, 4 pages.
(Continued)

*Primary Examiner* — Anita Nassiri-Motlagh
(74) *Attorney, Agent, or Firm* — Nixon & Vanderhye (57) ABSTRACT

A particulate material for removing an acid gas and/or mercury contaminant from a hydrocarbon gas is disclosed. The particulate material comprises a superabsorbent hydrogel comprising a cross-linked hydrophilic polymer network having from 0.1 mol % to 50 mol % cross-linking agent. The superabsorbent hydrogel has one or more compounds capable of binding the acid gas and/or mercury contaminant incorporated into the hydrophilic polymer network by absorbing said one or more compounds as a liquid phase or an aqueous solution. Methods for preparing the particulate material and using the particulate material to remove one or more acid gas and/or mercury contaminants from a hydrocarbon gas, dehydrating the hydrocarbon gas, and mitigating corrosion in gas flowlines are also disclosed.

25 Claims, 3 Drawing Sheets

(51) Int. Cl.
*B01D 53/14* (2006.01)
*B01J 20/22* (2006.01)
*B01J 20/28* (2006.01)
*B01J 20/30* (2006.01)
*B01J 20/32* (2006.01)
*C07C 7/12* (2006.01)
*C10L 3/10* (2006.01)

(52) U.S. Cl.
CPC .......... *B01D 53/1493* (2013.01); *B01J 20/22* (2013.01); *B01J 20/28004* (2013.01); *B01J 20/28016* (2013.01); *B01J 20/28047* (2013.01); *B01J 20/3085* (2013.01); *B01J 20/321* (2013.01); *B01J 20/3214* (2013.01); *B01J 20/3287* (2013.01); *B01J 20/3293* (2013.01); *C07C 7/12* (2013.01); *C10L 3/103* (2013.01); *C10L 3/104* (2013.01); *B01D 2252/20484* (2013.01); *B01D 2253/202* (2013.01); *B01D 2253/25* (2013.01); *B01D 2256/245* (2013.01); *B01D 2257/504* (2013.01); *B01D 2257/602* (2013.01); *C10L 2290/542* (2013.01)

(58) Field of Classification Search
CPC .. B01J 20/3085; B01J 20/321; B01J 20/3214; B01J 20/3287; B01J 20/3292; B01J 20/3293; B01D 53/02; B01D 53/1475; B01D 53/1493; B01D 2252/20484; B01D 2252/202; B01D 2252/25; B01D 2256/245; B01D 2257/504; B01D 2257/602; C10L 3/103; C10L 3/104; C10L 2290/542

USPC ........................................................ 252/184
See application file for complete search history.

(56)      References Cited

FOREIGN PATENT DOCUMENTS

| WO | WO 2010/011016 | 1/2010 |
| WO | 2016/024633 | 2/2016 |
| WO | 2016/187672 | 12/2016 |

OTHER PUBLICATIONS

Written Opinion of the IPEA for PCT/AU2017/051294 dated Oct. 22, 2018, 6 pages.
International Preliminary Report on Patentability for PCT/AU2017/051294 dated Dec. 20, 2018, 28 pages.
Y. Seo et al., "Preventing Gas Hydrate Agglomeration with Polymer Hydrogels", Energy & Fuels, Jun. 26, 2014, vol. 28, pp. 4409-4420.
J. Park et al., "Performance of Polymer Hydrogels Incorporating Thermodynamic and Kinetic Hydrate Inhibitors", Energy & Fuels, Mar. 21, 2016, vol. 30, pp. 2741-2750.
Y. Hoshino et al., "Reversible Absorption of $CO_2$ Triggered by Phase Transition of Amine-Containing Micro- and Nanogel Particles", Journal of the American Chemical Society, Oct. 23, 2012, vol. 134(44), pp. 18177-18180.
Search Report issued in EP Appln, No. 17873749.0 dated May 29, 2020.

* cited by examiner

PARTICULATE MATERIAL AND A METHOD FOR REMOVING ONE OR MORE CONTAMINANTS FROM HYDROCARBON GAS

This application is the U.S. national phase of International Application No. PCT/AU2017/051294 filed Nov. 23, 2017 which designated the U.S. and claims priority to AU Patent Application No. 2016904850 filed Nov. 25, 2016, the entire contents of each of which are hereby incorporated by reference.

TECHNICAL FIELD

The present disclosure generally relates to a particulate material and a method for removing one or more contaminants from hydrocarbon gas, such as natural gas. The contaminant may be mercury or a sour gas contaminant. In particular, the present disclosure relates to a method for preventing hydrate formation in natural gas streams. The present disclosure also relates to a method for reducing corrosion in gas pipelines.

BACKGROUND

The following discussion of the background to the invention is intended to facilitate an understanding of the invention. However, it should be appreciated that the discussion is not an acknowledgement or admission that any of the particulate material referred to was published, known or part of the common general knowledge as at the priority date of the application.

There are significant global natural gas reserves that include sour gas contaminants such as carbon dioxide ($CO_2$) and hydrogen sulphide ($H_2S$). Sub-quality natural gas reserves are defined as gas fields containing more than 2% $CO_2$, 4% $N_2$ and 4 parts per million (ppm) $H_2S$ (Kidnay and Parrish, 2006).

It is important to remove $CO_2$ as well as $H_2S$ from natural gas for several reasons. Firstly, these sour gases form acids in the presence of water and present a significant risk of corrosion to pipelines and processing equipment.

Secondly, non-combustible contaminants, such as $CO_2$ and $H_2S$, dilute and thereby reduce the calorific value of the gas. Accordingly, the maximum level of $CO_2$ permitted in natural gas transmitted to customers by pipeline is typically less than 3% (Hubbard, 2010).

With respect to LNG production or recovery of liquefied petroleum gas (LPG), the allowable $CO_2$ concentration of the natural gas should be less than 50 ppmv (Hubbard, 2010) prior to cooling the natural gas to cryogenic temperatures (as low as −161° C.) to avoid solidification of $CO_2$ and the formation of blockages in heat exchangers and other processing equipment. Similarly, it is important to remove other contaminants which are capable of freezing at these cryogenic temperatures, including water, heavier paraffinic hydrocarbons and aromatics such as benzene.

Natural gas processing and LNG production include the following steps: initial removal of liquids and solids in a slug catcher; gas compression; removal of acid gases (sweetening); gas dehydration; mercury removal; recovery of LPG/NGL; hydrocarbon dewpoint control; nitrogen rejection; outlet compression; and finally liquefaction. Depending on the markets and feed gas properties all of these steps may not be required.

Conventional gas sweetening methods include physical and chemical adsorption processes. These processes require a relatively high energy input for absorbent regeneration and consequently occupy a considerable environmental and spatial footprint in the gas processing plant. As gas recovery moves to remote and/or offshore locations, the reduction of capital and operational costs as well as spatial footprint becomes increasingly important.

Thus, there is a need to develop alternative and more efficient particulate materials and processes for removal of contaminants from natural gas.

SUMMARY

The present disclosure provides a particulate material and a method for removing one or more contaminants from a hydrocarbon gas, in particular natural gas. The present disclosure also provides respective methods for reducing corrosion in gas pipelines.

In one aspect of the disclosure there is provided a particulate material for removing an acid gas and/or mercury contaminant from a hydrocarbon gas. The particulate material comprises a superabsorbent hydrogel comprising a cross-linked hydrophilic polymer network having from 0.1 mol % to 50 mol % cross-linking agent. The amount of cross-linking agent may be governed by the physical robustness required of the superabsorbent hydrogel to function within a hydrocarbon gas stream and to enable spent particulate material (i.e. contaminant-loaded particulate material) to undergo one or more regeneration processes. In some particular embodiments, the amount of cross-linking agent may be at least 1.0 mol %, in particular at least 3 mol %, even more particularly at least 8 mol %, and yet even more particularly at least 15 mol %.

The superabsorbent hydrogel may swell and retain from 50 wt % to 99 wt % water, and more particularly from 85 wt % to 98 wt % water. It will be appreciated that the particulate material may comprises the superabsorbent hydrogel in a partially dehydrated state.

In one embodiment, the superabsorbent hydrogel may incorporate one or more compounds and/or chemical moieties capable of binding the acid gas and/or mercury contaminant. Incorporation may be achieved by absorbing the one or more compounds into the superabsorbent hydrogel. For example, a liquid phase of the one or more compounds or an aqueous solution of the one or more compounds may be absorbed into the superabsorbent hydrogel.

In one particular embodiment, the superabsorbent hydrogel, in a fully or partially dehydrated state, may comprise:
 a) 0.01 to 5 wt %, preferably 0.05 to 5 wt %, more preferably 0.1 to 4 wt % cross-linked hydrophilic polymer;
 b) 0 to 90 wt %, preferably 0.5 to 60 wt %, more preferably 10 to 50 wt % water; and
 c) 99 to 10 wt %, preferably 95 to 40 wt %, and more preferably 90 to 50 wt % of one or more compounds capable of binding the acid gas and/or mercury contaminant.

Within this embodiment, the superabsorbent hydrogel compositions cover a range of applications, including for example (i) a superabsorbent hydrogel with MEA (or similar) liquid absorbed therein (with no water) for dehydration and acidic gas absorption of the hydrocarbon gas stream; (ii) a superabsorbent hydrogel with a concentrated MEA aqueous solution absorbed therein for dehydration and acid gas absorption of the hydrocarbon gas stream; and (iii) superabsorbent hydrogel incorporated with a dilute MEA solution for predominantly absorbing acidic gases from the hydrocarbon gas stream.

In a particularly preferred embodiment of the present invention there is provided use of a superabsorbent hydrogel for removing acidic gases and water from a hydrocarbon gas, wherein the hydrocarbon gas comprises at least 20 wt % hydrocarbon compounds, wherein the hydrogel comprises:

a) 0.01 to 5 wt % cross-linked hydrophilic polymer network having from 0.1 mol % to 50 mol % cross-linking agent, wherein the hydrophilic polymer network is derivable from the group consisting of CMC-PAM-co-AA N-Cyclohexyl-N-(2-morpholinoethyl)carbodiimide (CMC), polyacrylic acid (AA) and/or polyacrylamide (PAM));
b) 99 to 10 wt % of an acid gas absorbent selected from the group consisting of monoethanolamine, diethanolamine, methyldiethanolamine, diisopropanolamine, and/or aminoethyoxyethanol; and optionally
c) 0 to 90 wt % water, wherein the acid gas absorbent and optionally water are absorbed into the superabsorbent hydrogel. Preferably, the cross-linked hydrophilic polymer network comprises, and preferably consists of, PAM-co-AA that is functionalised with 1-ethyl-3-(3-dimethylaminopropyl)carbodiimide (EDC) and then N-hydroxysuccinimide (NHS) to generate a NHS-functionalized PAM-co-AA where the NHS has been reacted with the acrylic acid groups, the NHS groups are crosslinked with 0.1 mol % to 50 mol % cross-linking agent consisting of a multi-functional amine (amine group ≥2).

A partially dehydrated superabsorbent hydrogel may be produced in a regeneration process, as later described. In some embodiments, retention of some residual water in the superabsorbent hydrogel is desirable so as to maintain the one of more compounds capable of binding the acid gas and/or mercury contaminant in solution. In other embodiments, the dehydration of the superabsorbent hydrogel may result in the formation of salt particles within the superabsorbent hydrogel which, in use, reabsorb moisture from the hydrocarbon gas stream to produce an aqueous solution of the salt within the superabsorbent hydrogel.

Additionally, the superabsorbent hydrogel when in a partially dehydrated state is expected to absorb the acid gas and/or mercury contaminant at a greater rate than a fully dehydrated superabsorbent hydrogel. Alternatively, based upon the relative proportion of water and other contaminants being removed with the superabsorbent hydrogel, it may not be necessary to entirely remove the water from the contaminant-loaded superabsorbent hydrogel to afford the regenerated superabsorbent hydrogel with sufficient absorbent capacity to remove the required amount of moisture from the hydrocarbon stream.

In one embodiment, the one or more compounds may be a liquid capable of absorbing an acid gas. The liquid may be capable of absorbing the acid gas by a chemical process or a physical process.

Suitable liquids that are capable of absorbing the acid gas by a chemical process include, but are not limited to, alkanolamines, alkylamines, alkyloxyamines, piperidine and its derivatives, piperazine and its derivatives, pyridine and its derivatives, and mixtures thereof.

Suitable liquids that are capable of absorbing the acid gas by a physical process include but are not limited to polyethylene glycol-dimethyl ethers (Selexol), N-methylpyrrolidone, propylene carbonate, methanol, sulfolane, imidazoles, ionic liquids, primary amines, secondary amines, tertiary amines, sterically hindered amines, and mixtures thereof.

In view of the fact that the superabsorbent hydrogel retains water within said polymer network, it will be appreciated that the liquids described above may be present in the superabsorbent hydrogel as aqueous solutions thereof.

In other embodiments, the one or more compounds may be incorporated in the superabsorbent hydrogel as an aqueous solution capable of absorbing an acid gas. In this particular embodiment the one or more compounds may comprise an inorganic salt which is soluble in aqueous solution. Aqueous inorganic salt solutions capable of absorbing acid gas include but are not limited to alkali or alkaline earth metal carbonate solutions, alkali or alkaline earth metal hydroxide solutions, or alkali or alkaline earth metal phosphate solutions.

Accordingly, in some embodiments the one or more compounds comprises an acid gas absorbent selected from the group consisting of an alkanolamine, alkylamine, alkyloxyamines, piperidine and its derivatives, piperazine and its derivatives, pyridine and its derivatives, polyethylene glycol-dimethyl ethers (Selexol), N-methylpyrrolidone, propylene carbonate, methanol, sulfolane, imidazoles, ionic liquids, primary amines, secondary amines, tertiary amines, sterically hindered amines, and mixtures of one or more of the preceding liquids, alkali or alkaline earth metal carbonate solutions, alkali or alkaline earth metal hydroxide solutions, or alkali or alkaline earth metal phosphate solutions.

In one particular embodiment, the particulate material comprises a superabsorbent hydrogel comprising a functionalised crosslinked polymer comprising PAM-co-AA that has been crosslinked with EDC, NHS and multifunctional amines, and an acid gas absorbent selected from the group consisting of monoethanolamine, diethanolamine, methyldiethanolamine, diisopropanolamine, and/or aminoethyoxyethanol.

In another embodiment the superabsorbent hydrogel may alternatively or additionally incorporate one or more chemical moieties capable of binding an acid gas and/or mercury contaminant. Incorporation of the one or more chemical moieties into the hydrogel may be achieved by covalently bonding or physically bonding the one or more chemical moieties to the cross-linked hydrophilic polymer network of the superabsorbent hydrogel.

In this particular embodiment, the chemical moiety may be derived from a monomer having one or more functional groups capable of binding to, or reacting with, the acid gas and/or mercury contaminant when the monomer is copolymerised or crosslinked to the polymer network. Suitable monomers for binding with an acid gas may be aminoalkylacrylamides, wherein the amino group is capable of binding to, or reacting with the acid gas contaminant. Illustrative examples of suitable aminoalklylacrylamides include but are not limited to aminpropylmethacrylate, am inopropylacrylate, aminoethylacrylate, ami nopropylmethacrylate hydrochloride, am inoethylmethacrylate, diethylacrylaminde, hydroxylmethylacrylamide.

Alternatively, the chemical moiety may be a group grafted onto said hydrophilic polymer network, or a cross-linking agent having one or more functional groups capable of binding to, or reacting with, an acid gas when the group is grafted onto the hydrophilic polymer network, or the cross-linking agent is crosslinked to the hydrophilic polymer network.

In some embodiments, the particulate material further comprises a hygroscopic salt incorporated into the cross-linked polymer network. The hygroscopic salt may be a monovalent salt such as lithium chloride or lithium bromide or a divalent salt, such as calcium chloride or calcium sulphate. The hygroscopic salt may be incorporated into the cross-linked polymer by absorption of an aqueous solution of the hygroscopic salt into the superabsorbent hydrogel. Alternatively, the superabsorbent hydrogel may be prepared in the presence of the hygroscopic salt. The hygroscopic salt may be present in the superabsorbent hydrogel in any amount up to saturation thereof.

In another aspect of the disclosure there is provided a method of preparing a particulate material for removing an acid gas and/or mercury contaminant from a hydrocarbon gas. The method may comprise contacting a superabsorbent hydrogel comprising a cross-linked hydrophilic polymer network of from 0.1 mol % to 50 mol % crosslinker with a liquid phase or an aqueous solution of one or more compounds capable of removing the acid gas and/or mercury contaminant, wherein the superabsorbent hydrogel absorbs the liquid phase or the aqueous solution within the cross-linked hydrophilic polymer network.

Alternatively, the particulate material may be prepared by dehydrating a superabsorbent hydrogel comprising a cross-linked polymer network of from 0.1 mol % to 50 mol % crosslinker having a liquid phase or an aqueous solution of one or more compounds capable of removing the acid gas and/or mercury contaminant incorporated within the cross-linked polymer network.

In one embodiment, a weight percentage of the one or more compounds in the particulate material may be controlled by varying the concentration of the one or more compounds in the aqueous solution or varying the dehydration conditions. The concentration of the one or more compounds in the aqueous solution may be selected to afford a desired weight percentage of the one or more compounds in the particulate material. In some embodiments, the concentration of the one or more compounds in the aqueous solution may be from 2 wt % to 95 wt %, from 5 wt % to 70 wt % and more particularly from 10 wt % to 65 wt %.

Alternatively, the weight percentage of the one or more compounds in the absorbent may be controlled by varying a period of time the superabsorbent hydrogel contacts the liquid phase or the aqueous solution or varying a period of time that the superabsorbent hydrogel is dehydrated.

In some embodiments, the absorbent may be prepared by contacting the superabsorbent hydrogel with a first liquid or aqueous solution of a first compound capable of removing a first acid gas and/or mercury contaminant to produce a partially swelled superabsorbent hydrogel having the first liquid or aqueous solution absorbed therein and subsequently contacting said partially swelled superabsorbent hydrogel with a second liquid or aqueous solution of a second compound capable of removing a second acid gas and/or mercury contaminant. The first or the second compound may be the hygroscopic salt.

In some embodiments, the method further comprises drying the swelled superabsorbent hydrogel.

In another aspect of the disclosure there is provided an alternative method of preparing a particulate material for removing one or more acid gas and/or mercury contaminants from a hydrocarbon gas.

The method comprises:
  (i) providing a first solution comprising:
    (a) a hydrophilic polymer having a repeating monomer unit comprising at least two different pendant functional groups;
    (b) a cross-linking agent having at least two pendant functional groups capable of forming a covalent bond with the hydrophilic polymer; wherein at least one of the at least two pendant functional groups of the repeating monomer unit or the cross-linking agent is capable of binding to or reacting with an acid gas and/or mercury contaminant,
  (ii) reacting the cross-linking agent with the polymer so that hydrogel particles comprising a cross-linked polymer having 0.1 mol % to 50 mol % cross-linked polymer network is formed,
  wherein a desired particle size is formed by either:
    (A) suspending the first solution within a second solution, wherein the first solution is immiscible with the second solution, then subsequently reacting the cross-linking agent with the polymer; or
    (B) freeze drying the cross-linked polymer; and then comminuting the freeze dried cross-linked hydrophilic polymer to form dried superabsorbent hydrogel particles of a desired size.

In one embodiment, at least one of the at least two pendant functional groups of the repeating monomer is a carboxyl or activated carboxylate group and the cross-linking agent is capable of forming a covalent bond with the carboxyl or activated carboxylate group.

In an alternative embodiment, the cross-linking agent is a multifunctional vinyl monomer or a cross-linking monomer capable of forming a covalent bond with the hydrophilic polymer by a radical-initiated cross-linking reaction.

In one embodiment, the desired particle size of the superabsorbent hydrogel particles in process A is determined by controlling droplet size of the first solution in the second solution. The droplet size may vary from 100 μm to 1 mm in diameter. Controlling the droplet size of the first solution in the second solution may comprise varying a stirring speed of the first solution and the second solution. Alternatively, controlling the droplet size of the first solution in the second solution may comprise adding a surfactant to the first solution and the second solution.

In one embodiment, the method may further comprise the step of adding a functionalised agent, the functionalised agent containing at least one pendant functional group capable of forming a covalent bond with a carboxyl or activated carboxylate group on the cross-linked polymer or with the multifunctional vinyl monomer on the cross-linked polymer. The functionalised agent may be a polymer or other organic molecule. In preferred embodiments, the pendant functional group on the functionalised agent may be a primary amine.

In another aspect of the disclosure there is provided a method for removing one or more acid gas and/or mercury contaminants from a hydrocarbon gas. The hydrocarbon gas may comprise at least 20 wt % hydrocarbon compounds, in particular at least 50 wt % hydrocarbon compounds.

Said method comprises contacting a hydrocarbon gas with a particulate superabsorbent hydrogel material comprising a cross-linked hydrophilic polymer network having from 0.1 mol % to 50 mol % cross-linking agent, wherein said polymer network incorporates one or more compounds or chemical moieties capable of binding an acid gas and/or mercury contaminant.

The step of contacting may comprise passing a stream of hydrocarbon gas through a bed of particulate superabsorbent hydrogel material. The bed may be a stationary bed or a moving bed.

Alternatively, the step of contacting may comprise introducing into a hydrocarbon gas stream a flow of particulate superabsorbent hydrogel material.

In this particular embodiment, contaminant-loaded superabsorbent hydrogel may be separated downstream, for example by filtration or centrifugation, after isolation from the hydrocarbon gas stream in a slug catcher. Said separated superabsorbent hydrogel may then undergo one or more regeneration processes and be subsequently reintroduced upstream into the hydrocarbon gas stream.

Accordingly, at least a portion of the regenerated particulate superabsorbent hydrogel material may be recycled upstream.

The regenerated particulate superabsorbent hydrogel material may have a higher weight percentage water saturation relative to a weight percentage saturation of the acid gas and/or mercury contaminant.

In another embodiment, the method for removing one or more acid gas and/or mercury contaminants from a hydrocarbon gas may comprise contacting the hydrocarbon gas with a first particulate superabsorbent hydrogel material and a second particulate superabsorbent hydrogel material.

Said first particulate superabsorbent hydrogel material may be described as herein and incorporate one or more compounds or chemical moieties capable of binding a first acid gas and/or mercury contaminant.

Said second particulate hydrogel superabsorbent material may be described as herein and incorporate one or more compounds or chemical moieties capable of binding a second acid gas and/or mercury contaminant. Said first contaminant may be the same or different to said second contaminant.

The hydrocarbon gas may be contacted with the first particulate superabsorbent hydrogel material and subsequently contacted with the second particulate superabsorbent hydrogel materials to sequentially remove the first and second contaminants.

Alternatively, the hydrocarbon gas may be contacted with a mixture of the first and second particulate superabsorbent hydrogel materials to remove the first and second contaminants.

The first or the second particulate superabsorbent hydrogel materials may be the regenerated particulate superabsorbent hydrogel material.

In another aspect of the disclosure there is provided a contaminant-loaded superabsorbent hydrogel comprising a cross-linked hydrophilic polymer network having from 0.1 mol % to 50 mol % cross-linking agent and one or more acid and/or mercury contaminants bound within said polymer network. The cross-linked hydrophilic polymer network may optionally incorporate one or more compounds or chemical moieties capable of binding the acid gas and/or mercury contaminant Accordingly, in some embodiments, the contaminant-loaded superabsorbent hydrogel may comprise cross-linked hydrophilic polymer network having from 0.1 mol % to 50 mol % cross-linking agent, one or more compounds or chemical moieties capable of binding an acid gas and/or mercury contaminant incorporated within said polymer network, water and an acid gas and/or mercury contaminant. The particulate material as described herein is capable of absorbing free water, thereby preventing agglomeration and deposition of methane hydrates in flowlines for transport of hydrocarbon gas. Accordingly, in a further aspect of the disclosure there is provided a method for mitigating hydrate formation in gas flowlines.

The method comprises introducing into a gas flowline a plurality of superabsorbent hydrogel particles comprising a cross-linked hydrophilic polymer network having from 0.1 mol % to 50 mol % cross-linking agent, wherein the superabsorbent hydrogel particles optionally incorporate one or more compounds or chemical moieties capable of binding an acid gas and/or mercury contaminant.

Furthermore, certain embodiments of the particulate material as described herein may be capable of absorbing acid gases in addition to free water, thereby reducing potential for corrosion in flowlines for transport of hydrocarbon gas and/or processing equipment. Accordingly, in a further aspect of the disclosure there is provided a method for mitigating corrosion in gas flowlines.

The method comprises introducing into a gas pipeline a particulate material comprising superabsorbent hydrogel particles comprising a cross-linked hydrophilic polymer network having from 0.1 mol % to 50 mol % cross-linking agent, wherein the superabsorbent hydrogel particles incorporate one or more compounds or chemical moieties capable of binding an acid gas and/or mercury contaminant other than water.

The particulate material as described herein may also be employed in a method for dehydrating a hydrocarbon gas. Said method comprises contacting a hydrocarbon gas with particulate superabsorbent hydrogel material comprising a cross-linked hydrophilic polymer network having from 0.1 mol % to 50 mol % cross-linking agent, wherein said polymer network optionally incorporates one or more compounds or chemical moieties capable of binding an acid gas and/or mercury contaminant.

Several uses for the superabsorbent hydrogels as described herein are envisaged.

In its broadest form, the disclosure provides a use of a superabsorbent hydrogel comprising a cross-linked hydrophilic polymer network having from 0.1 mol % to 50 mol % cross-linking agent for removing an acid gas and/or mercury contaminant from a hydrocarbon gas. The superabsorbent hydrogel may be as described previously and may incorporate one or more compounds or chemical moieties capable of binding an acid gas and/or mercury contaminant within said polymer network.

Accordingly, some embodiments relate to use of said superabsorbent hydrogel for removing water and, optionally, an acid gas and/or mercury contaminant, from a hydrocarbon gas.

Alternatively, other embodiments relate to use of said superabsorbent hydrogel for removing a contaminant other than water from a hydrocarbon gas. In particular the contaminant may be a sour gas.

Other embodiments relate to use of said superabsorbent hydrogel for mitigating hydrate formation in gas flowlines.

Still other embodiments relate to use of said superabsorbent hydrogel for mitigating corrosion in gas flowlines.

Still other embodiments relate to use of a superabsorbent hydrogel comprising a cross-linked hydrophilic polymer network having from 0.1 mol % to 50 mol % cross-linking agent for removing water from a hydrocarbon gas, wherein the superabsorbent hydrogel optionally incorporates one or more compounds or chemical moieties capable of binding an acid gas and/or mercury contaminant.

BRIEF DESCRIPTION OF DRAWINGS

Preferred embodiments of the present invention will now be further described and illustrated, by way of example only, with reference to the accompanying drawings in which.

DESCRIPTION OF EMBODIMENTS

The present disclosure generally relates to particulate material and a method for removing one or more contaminants from hydrocarbon gas, such as natural gas. The contaminant may be water or a sour gas contaminant. In particular, the present disclosure relates to a method for mitigating hydrate formation in natural gas streams. The present disclosure also relates to a method for reducing corrosion in a gas processing plant and/or flowlines.

General Terms

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or groups of compositions of matter. Thus, as used herein, the singular forms "a", "an" and "the" include plural aspects unless the context clearly dictates otherwise. For example, reference to "a" includes a single as well as two or more; reference to "an" includes a single as well as two or more; reference to "the" includes a single as well as two or more and so forth.

Each example of the present disclosure described herein is to be applied mutatis mutandis to each and every other example unless specifically stated otherwise. The present disclosure is not to be limited in scope by the specific examples described herein, which are intended for the purpose of exemplification only. Functionally-equivalent products, compositions and methods are clearly within the scope of the disclosure as described herein.

The term "and/or", e.g., "X and/or Y" shall be understood to mean either "X and Y" or "X or Y" and shall be taken to provide explicit support for both meanings or for either meaning.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Unless otherwise defined, all technical and scientific terms used herein have the same meaning as commonly understood by one of ordinary skill in the art to which this invention belongs. Although methods and particulate materials similar or equivalent to those described herein can be used in the practice or testing of the present invention, suitable methods and particulate materials are described below. In case of conflict, the present specification, including definitions, will control. In addition, the particulate materials, methods, and examples are illustrative only and not intended to be limiting.

Specific Terms

The term 'particulate' refers to the form of discrete solid units. The units may take the form of flakes, fibres, agglomerates, granules, powders, spheres, pulverized materials or the like, as well as combinations thereof. The particles may have any desired shape including, but not limited to, cubic, rod like, polyhedral, spherical or semi-spherical, rounded or semi-rounded, angular, irregular, and so forth.

The term 'hydrocarbon gas' as used herein refers to a gas mixture whose composition may vary significantly but which will include alkanes, predominantly methane, ethane and higher molecular weight hydrocarbons (C3+), water and other contaminants including, but not limited to, acid gases, nitrogen, mercury, and freezable organic compounds. The term 'acid gas' means any one or more of carbon dioxide, hydrogen sulphide, carbon disulphide, carbonyl sulphide, mercaptans (R-SH, where R is an alkyl group having one to 20 carbon atoms), sulphur dioxide, and aromatic sulphur-containing compounds. The term 'freezable organic compounds' refers to an organic compound which is capable of solidifying at various operating temperature ranges employed in natural gas processing, in particular cryogenic temperatures employed in production of liquefied natural gas. Illustrative examples of freezable organic compounds include aromatic hydrocarbons such as benzene, toluene, xylene, naphthalenes and so forth.

The term 'hydrocarbon gas' will be used throughout to refer to a gaseous mixture of hydrocarbon compounds including, but not limited to methane, ethane, ethylene, propane, iso-propane, and other C3+ hydrocarbons. In some embodiments, the hydrocarbon gas comprises at least 20 wt % hydrocarbon compounds although in other embodiments the hydrocarbon gas comprises at least 50 wt % hydrocarbon compounds. Although the term 'hydrocarbon gas' will be used throughout the description as a reference to natural gas, it will be appreciated by those skilled in the art that the term may equally apply to coal seam gas, associated gas, non-conventional gas, landfill gas, biogas, and flue gas.

The term 'superabsorbent hydrogel' as used herein refers to a cross-linked hydrophilic polymeric material that is capable of absorbing and retaining under moderate pressure large amounts of an aqueous liquid relative to its mass. Typically, a superabsorbent hydrogel is capable of absorbing at least 20 times its own weight in fluid and up to 300 times its own weight in fluid, preferably 50 g/g up to 200 g/g, in particular from 100 g/g to 150 g/g. The absorbed liquid is taken into the polymeric network of the superabsorbent hydrogel through hydrogen bonding rather than being contained in pores from which the fluid could be eliminated by squeezing. While they are compatible with aqueous environments, superabsorbent hydrogels do not dissolve in water.

The term 'partially dehydrated' as used herein refers to a superabsorbent hydrogel having from 0.5 to 60 wt % water content, more preferably 10 to 50 wt % water content.

The term 'cross-linked polymer network' as used herein refers to a region in a polymeric material in which the polymer chains are covalently or physically bonded to one another by means of crosslinking agents. The density or degree of crosslinking within a polymeric material may be measured and/or calculated according to conventional experiments associated with the swelling capacity of the polymeric material, such as in accordance with ASTM standards D2765 or F2214. Typically, a more tightly cross-linked polymer network will be capable of absorbing less fluid than a loosely cross-linked polymer network. Furthermore, the density or degree of crosslinking within a polymeric material may be tunable by conventional techniques as will be well understood by one skilled in the art.

The term "modulus of elasticity" or "modulus," as used herein, refers to Young's modulus of elasticity, a standard measure of elasticity known to persons of ordinary skill in the art. The unit for expressing "modulus" or "modulus of elasticity" is the pascal (Pa), a unit known to persons of ordinary skill in the art (1 pascal=1 N/m$^2$, where N=Newton and m=meter). A practical unit used in this application is the megapascal (MPa; 1 MPa=1×106 Pa). 1 MPa is approximately equal to 102 g/mm$^2$ or 1×107 dynes/cm$^2$. As it pertains to this application, modulus is measured and expressed for fully hydrated superabsorbent hydrogel material, unless otherwise specified.

The expression 'capable of binding an acid gas and/or mercury contaminant' as used herein refers to a characteristic of a compound or chemical moiety which allows said compound or chemical moiety to selectively bind the acid gas and/or mercury contaminant. For example, the acid gas and/or mercury contaminant may selectively bind to the compound or chemical moiety by means of a chemical process, such as by formation of chemical bonds (e.g. covalent, ionic, hydrogen bonds) or by a physical process, such as by solvation.

Particulate Material

The present disclosure generally relates to a particulate material for removing one or more contaminants from hydrocarbon gas, such as natural gas. The contaminant may be an acid gas, such as $CO_2$ or $H_2S$ and/or mercury.

The particulate material comprises a superabsorbent hydrogel comprising a cross-linked hydrophilic polymer network having from 0.1 mol % to 50 mol % cross-linker. A lower cross-linker content may potentially result in the superabsorbent hydrogel falling apart, whereas a higher cross-linker content may potentially result in the superabsorbent hydrogel becoming too rigid. In one particular embodiment, the cross-linked hydrophilic polymer network may have from 0.01 mol % to 20 mol % cross-linker.

The swelling ability of the superabsorbent hydrogel is also dependent on the nature of the cross-linked polymer network. For example, a superabsorbent hydrogel with a long hydrophilic cross-links swells more than an analogous cross-linked polymer network with short hydrophobic cross-links.

The hydrophilic polymer content of the superabsorbent hydrogel is in part selected to provide suitable mechanical and chemical properties to the particulate material. The particulate material needs to be able to withstand an industrial processing environment, in particular a gas processing environment. The superabsorbent hydrogel needs to be physically robust so that it can be introduced into a gas flowline as a flow of particulate material (see below) or so that the particulate material can be provided in a packed bed with sufficient interstitial space between adjacent particles to allow a flow of gas therethrough. The superabsorbent hydrogel also needs to be able to withstand a wide temperature range, in particular when undergoing thermal regeneration. Furthermore, the cross-linked polymer network of the superabsorbent hydrogel needs to be chemically inert in the chemical environment.

In some embodiments, the superabsorbent hydrogel comprises a cross-linked hydrophilic polymer comprising a plurality of homogenous hydrophilic polymers selected from the synthetic (derived from hydrocarbons) group consisting of polyacrylic acid, hydrolyzed polyacrylamide or polyacrylamide-co-acrylic acid, polyacrylamide-co-acrylic acid partial sodium salt, poly(acrylic acid-co-maleic acid), poly(N-isopropylacrylamide, polyethylene glycol, polyethyleneimine, polyallylamine and vinylpyrrolidone. Alternatively, the superabsorbent hydrogel can be formed using natural polymers such as polysaccharides, chitin, polypeptide, alginate or cellulose.

In some embodiments, the cross-linked hydrophilic polymer includes a functionalised agent, the functionalised agent containing at least one pendant functional group having formed a covalent bond with a carboxyl or activated carboxylate group on the cross-linked polymer. The functionalised agent may be a polymer or other organic molecule. In some embodiments, the resulting polymer contains a succinimide ester derivative group that can be both cross-linked and functionalised as described above to form a functionalised cross-linked polymer network. Similarly, as above the degree of functionalisation of the cross-linked hydrophilic polymer network can be readily controlled by changing the level of activation of the polymer. This functionalisation is described in more detail in the detailed description below.

The superabsorbent hydrogel is selected to be capable of swelling with water and retaining from 50 wt % to 99 wt % water, more particularly from 85 wt % to 98 wt % water. Accordingly, the superabsorbent hydrogel may be selected from the group consisting of hydrophilic polymers containing carboxy groups such as polyacrylic acid, hydrolyzed polyacrylamide or polyacrylamide-co-acrylic acid, polyacrylamide-co-acrylic acid partial sodium salt, and poly(acrylic acid-co-maleic acid) or poly(N-isopropylacrylamide, polyvinyl N-vinyl caprolactam such as polyvinylcaprolactam, vinylpyrrolidone, and vinylcaprolactam covalently bonded together.

In exemplary embodiments, the superabsorbent hydrogel comprises a functionalised crosslinked polymer comprising PAM-co-AA that has been crosslinked with EDC, NHS and multifunctional amines.

A final modulus of the superabsorbent hydrogel after cross-linking can be from 0.1 Pa to 12000 Pa as measured by rheological techniques described herein.

In various embodiments, the final modulus of the superabsorbent hydrogel after cross-linking may be at least 0.1, in particular at least 10, more particularly at least 30, even more particularly at least 50 and yet even more particularly at least 100 Pa.

In various embodiments, the final modulus of the superabsorbent hydrogel after cross-linking may be no more than 12,000, in particular no more than 10,000, more particularly no more than 8000 and yet even more particularly no more than 6000 Pa.

In some embodiments, the final modulus of the superabsorbent hydrogel after cross-linking can be from 0.2 Pa to 12000 Pa, in particular from 0.2 Pa to 10000 Pa, more particularly from 0.2 Pa to 5000 Pa, even more particularly from 1 Pa to 12000 Pa, yet more particularly from 1 Pa to 10000 Pa as measured by rheological techniques.

In some embodiments, the final modulus of the superabsorbent hydrogel after cross-linking can be from 10 Pa to 12000 Pa, more particularly from 10 Pa to 10000 Pa, yet more particularly 100 Pa up to 10000 Pa as measured by rheological techniques described herein.

In other embodiments, the final modulus of the superabsorbent hydrogel after cross-linking can be from 0.1 Pa up to 10000 Pa, in particular from 0.1 Pa to 5000 Pa, from 0.1 Pa to 1000 Pa, more particularly from 1 Pa to 12000 Pa, more particularly from 1 Pa to 10000 Pa, more particularly from 100 Pa to 12000 Pa, yet more particularly from 500 Pa to 12000 Pa, yet more particularly from 1000 Pa to 12000 Pa as measured by rheological techniques described herein.

In other embodiments, the final modulus of the superabsorbent hydrogel after cross-linking can be from 1 Pa to 5000 Pa, more particularly from 10 Pa to 5000 Pa, yet more particularly from 100 Pa to 5000 Pa as measured by rheological techniques described herein.

In some embodiments, the final modulus of the superabsorbent hydrogel after cross-linking is no more than 9,000, more particularly no more than 5,000, even more preferable no more than 4000 as measured by rheological techniques described herein.

Whilst a number of rheological techniques can be used to determine the modulus of a superabsorbent hydrogel, it should be understood that rheological techniques refers to rheology measurements of a superabsorbent hydrogel, typically in bulk form, using a Rheometer, for example a HR-3 Discovery Hybrid Rheometer (TA Instruments). A Rheometer can be used to control shear stress or shear strain and/or apply extensional stress or extensional strain and thereby determine mechanical properties of a hydrogel including the modulus of elasticity thereof.

The particulate material may be self-supporting. The term 'self-supporting' as used herein refers to the ability of discrete particles in the particulate material to maintain their morphology in the absence of a support material. The particulate material may be of any suitable size and/or shape and/or morphology. In one embodiment, the particulate material may have an average particle size in a range from about 10 μm to about 2000 μm with a standard deviation of ±20%. In another embodiment, the particulate material may have an average particle size from about 10 μm to about 1000 μm. As used herein, the term 'average particle size' refers to the volume-based mean particle size.

Illustrative examples of suitable morphologies include, but are not limited to, beads, sheets, cast blocks, cylinders, discs and porous membranes. Morphologies which allow the particulate material to flow are particularly preferred. In one particular embodiment, the particulate material may be in the form of beads.

The beads may have a controlled particle size and can maintain their morphology in a range of different environments and shear conditions. In some embodiments the beads may have one or more of the following properties: a mean length diameter of 10 to 2000 μm; a cross-link density of ≥1 mol %; a maximum cross-link density of 40 mol %; a mean length diameter of 10 to 2000 μm; are mechanically robust and remain intact in conditions where methane hydrate formation may occur; are sufficiently mechanically flexible to allow swelling; are stable in different chemical environments, such as in the presence of condensed hydrocarbon liquids and gases such as nitrogen and carbon dioxide; are hydrophilic and are able to contain >75% by weight water. In particular, the beads may tolerate high shear rates.

In some alternative embodiments, the particulate material may be a composite material comprising an inert particulate material coated with the superabsorbent hydrogel as described herein. Illustrative examples of inert particulate materials include, but are not limited to, alumina, silica, aluminosilicates, silicon carbide, ceramics, metal oxides, refractory materials, inert polymeric materials.

In a still further alternative embodiment, the superabsorbent hydrogel as described herein may be coated on a ceramic monolith having sufficient porosity therein to allow flow of a hydrocarbon gas therethrough.

The cross-linked hydrophilic polymer network of the superabsorbent hydrogel exhibits the ability to swell and retain a significant amount of water within its structure without dissolving in water. The superabsorbent hydrogel may swell in response to water and retain from 50 wt % to 99 wt % water, in particular from 85 wt % to 98 wt % water. Accordingly, the superabsorbent hydrogel uses this inherent characteristic to absorb aqueous or hydrophilic fluids to incorporate one or more compounds capable of binding an acid gas and/or mercury contaminant.

In one embodiment incorporation of the one or more compounds in the superabsorbent hydrogel may be achieved by absorbing the one or more compounds into the superabsorbent hydrogel. For example, a liquid phase of the one or more compounds may be absorbed into the superabsorbent hydrogel, in particular a hydrophilic liquid phase of the one or more compounds. Alternatively, an aqueous solution of the one or more compounds may be absorbed into the superabsorbent hydrogel.

In particular, the one or more compounds may be capable of absorbing an acid gas. The one or more compounds may be capable of absorbing the acid gas by a chemical process or a physical process.

For example, a liquid phase of the one or more compounds capable of absorbing an acid gas may be a chemical solvent, in particular an alkanolamine compound such as diethanoloamine (DEA), monoethanolamine (MEA), methyldiethanolamine (MDEA), diisopropanolamine (DIPA) and aminoethoxyethanol (diglycolamine)(DGA).

Suitable liquids that are capable of absorbing the acid gas by a chemical process include but are not limited to alkanolamines, alklyamines, piperidine and its derivatives, piperazine and its derivatives, pyridine and its derivatives. Suitable liquids that are capable of absorbing the acid gas by a physical process include but are not limited to polyethylene glycol-dimethyl ethers (Selexol), N-methylpyrrolidone, propylene carbonate, sulfolane, imidazoles and ionic liquids. Aqueous inorganic salt solutions capable of absorbing the acid gas include but are not limited to carbonate solutions or phosphate solutions.

In other forms the liquid phase of the one or more compounds may be a physical solvent, in particular a solvent which has a high absorptive capacity for the acid gas. Illustrative examples of suitable physical solvents include, but are not limited to aqueous potassium carbonate, polyethylene glycol-dimethyl ether, N-methylpyrrolidone, propylene carbonate, sulfolane and so forth. It will be appreciated by those skilled in the art that the superabsorbent hydrogel may incorporate one or more chemical and/or physical solvents, provided that the solvents are not incompatible with each other or the superabsorbent hydrogel.

Other suitable compounds capable of binding or absorbing an acid gas are described in May's review: *The removal of $CO_2$ and $N_2$ from natural gas: A review of conventional and emerging process technologies*, T. E. Rufford et al./Journal of Petroleum Science and Engineering 94-95 (2012) 123-154

Alternatively, incorporation of the one or more chemical moieties into the superabsorbent hydrogel may be achieved by physically or covalently bonding the one or more chemical moieties to the cross-linked polymer network. Such chemical moieties may be selected from amine or alkoxide functional groups. Illustrative examples of suitable chemical moieties capable of binding an acid gas, wherein the chemical moieties may be covalently bonded to the cross-linked polymer network include, but are not limited to, diethylenetriamine, tetraethylenepentamine, monoethanolamine, diethanolamine, triethanolamine and so forth.

In another embodiment, the chemical moiety may be derived from a monomer having one or more functional groups capable of binding to, or reacting with, an acid gas and/or mercury contaminant when the monomer is copolymerised or crosslinked to the polymer network. The monomer may have one or more functional group selected from amine or alkoxide functional groups. Illustrative examples of such monomers that may bind an acid gas contaminant include, but are not limited to am inoalkylacrylamide-based polymers such as aminopropylmethacrylate, am inopropylacrylate, aminoethylacrylate, aminopropylmethacrylate hydrochloride, aminoethylmethacrylamide, diethylacrylamide, hydroxylmethylacrylamide.

The inventor has found that the absorptive capacity of the particulate material as described herein may be enhanced by incorporating a hygroscopic salt into the cross-linked polymer network. Accordingly, the particulate material may further comprise a hygroscopic salt incorporated into the cross-linked polymer network. The hygroscopic salt may be a monovalent salt such as lithium chloride, lithium bromide or sodium chloride, or a divalent salt such as calcium chloride, calcium sulphate. The hygroscopic salt may be present in the cross-linked polymer network in any amount up to saturation thereof.

Methods of Preparing the Particulate Material

The particulate material for removing one or more contaminants from a hydrocarbon gas may be prepared according to various suitable methods.

Absorption of the Liquid Phase or the Aqueous Solution

In some embodiments the method may comprise contacting a superabsorbent hydrogel comprising a cross-linked polymer network of from 0.1 mol % to 50 mol % crosslinker with a liquid phase or an aqueous solution of one or more compounds capable of removing an acid gas and/or mercury contaminant, wherein the superabsorbent hydrogel absorbs the liquid phase or the aqueous solution within the cross-linked polymer network.

A weight percentage of the one or more compounds incorporated into the particulate material may be controlled by varying the concentration of the one or more compounds in the aqueous solution. The concentration of the one or more compounds in the aqueous solution may be selected to afford a desired weight percentage of the one or more compounds in the particulate material. In some embodiments, the concentration of the one or more compounds in the aqueous solution may be from 2 wt % to 95 wt %, in particular from 5 wt % to 70 wt % and more particularly from 10 wt % to 65 wt %.

Alternatively, the weight percentage of the one or more compounds in the particulate material may be controlled by varying a period of time the superabsorbent hydrogel contacts the liquid phase or the aqueous solution. The period of time the superabsorbent hydrogel contacts the liquid phase or the aqueous solution may vary from 60 seconds to 60 minutes, although this may depend on a maximum swelling rate of the superabsorbent hydrogel and the manner in which the superabsorbent hydrogel is contacted with the liquid phase or the aqueous solution. Generally, a rate at which the superabsorbent hydrogel will absorb the liquid phase or the aqueous solution will slow as the superabsorbent hydrogel approaches saturation.

In some embodiments, the particulate material may be prepared by contacting the superabsorbent hydrogel with a first liquid or aqueous solution to produce a partially swelled superabsorbent hydrogel having the first liquid or aqueous solution absorbed therein and subsequently contacting said partially swelled superabsorbent hydrogel with a second liquid or aqueous solution.

One or the other or both of the first and second liquids or aqueous solutions of one or more compounds capable of removing an acid gas and/or mercury contaminant from a hydrocarbon gas. In some embodiments, the first and/or second aqueous solution may be a hygroscopic salt, such as lithium chloride. Incorporation of the hygroscopic salt, in particular lithium chloride, has been shown to enhance the absorptive capacity of the particulate material with respect to water and other contaminants found in the hydrocarbon gas stream.

After incorporating the one or more compounds into the superabsorbent hydrogel, the method may further comprise drying the swelled superabsorbent hydrogel, in particular to remove excess water and/or control a concentration of the one or more compounds in the superabsorbent hydrogel.

Polymeric Synthesis

An alternative method of preparing a particulate material for removing one or more contaminants from a hydrocarbon gas comprises:

(i) providing a first solution comprising:
(a) a hydrophilic polymer having a repeating monomer unit comprising at least two different pendant functional groups;
(b) a cross-linking agent having at least two pendant functional groups capable of forming a covalent bond with the hydrophilic polymer;
wherein at least one of the at least two pendant functional groups of the repeating monomer unit or the cross-linking agent is capable of binding to or reacting with an acid gas and/or mercury contaminant,
(ii) reacting the cross-linking agent with the polymer so that hydrogel particles comprising a cross-linked polymer having 0.1 mol % to 50 mol % cross-linked polymer network is formed,
wherein a desired particle size is formed by either:
(A) suspending the first solution within a second solution, wherein the first solution is immiscible with the second solution, then subsequently reacting the cross-linking agent with the polymer; or
(B) freeze drying the cross-linked polymer; and then comminuting the freeze dried cross-linked polymer to form dried superabsorbent hydrogel particles of a desired size.

In one embodiment, at least one of the at least two pendant functional groups of the repeating monomer is a carboxyl or activated carboxylate group and the cross-linking agent is capable of forming a covalent bond with the carboxyl or activated carboxylate group.

The above method may further comprise the step of adding a functionalised agent to the first solution, the functionalised agent containing at least one pendant functional group capable of forming a covalent bond with a carboxyl or activated carboxylate group on the cross-linked polymer. The functionalised agent may be a polymer or other organic molecule. In preferred embodiments, the pendant functional group on the functionalised agent is a primary amine.

In yet other embodiments, the superabsorbent hydrogel is formed from monomers which are cross-linked using suitable techniques such as free radical chemistry. In some embodiments, superabsorbent hydrogels are formed using post-synthetic cross-linking of existing polymers. For example, the cross-linking agent may be a multifunctional vinyl monomer or a cross-linking monomer.

The cross-linking agent may comprise any suitable compound with the required pendant functional groups. In some embodiments, the pendant functional groups on the cross-linking agent are primary amines, in particular a diamine compound. In some embodiments, at least one of the at least two pendant functional group is an activated carboxylate group, formed by reacting the polymer with a carbodiimide, wherein the carbodiimide covalently bonds to the carboxyl group thereby forming the activated carboxylate group.

The first solution is preferably an aqueous solution, or a miscible aqueous-organic solvent solution. In some embodiments, the miscible aqueous-organic solvent solution comprises a solvent selected from the group consisting of tetrahydrofuran, isomers of propenol, methanol, ethanol, dioxane, dimethylsulfoximide, dimethylformamide, acetonitrile, acetone, acetic acid, or combinations thereof.

The second solution is preferably selected from the group consisting of toluene and straight chain $C_6$- to $C_8$-hydrocarbons, or combinations thereof. In some embodiments, the second solution further comprises a non-ionic surfactant selected from the group consisting of sorbitol esters cellulose butyrate acetate, hydroxyethyl cellulose, cellulose diacetate, 1-Oleoyl-rac-glycerol, 2-cyclohexylethyl β-D-maltoside, polyoxyethylene surfactants, cyclohexylmethyl β-D-maltoside, digitonin, ethylene glycol monododecyl ether, ethylene glycol monohexyl ether, ethylene glycol monooctadecyl ether, polyoxyethylene dodecyl ether, hexaethylene glycol monodecyl ether, Polyoxyethylene isooctylphenyl ether, nonaethylene glycol monododecyl ether, octaethylene glycol monodecyl ether, octaethylene glycol monotetradecyl ether, pentaethylene glycol monodecyl ether, pentaethylene glycol monohexadecyl ether, terpolymers of poly(ethylene glycol)-poly(propylene glycol)-poly(ethylene glycol), polyoxyethylene (20) oleyl ether, polyoxyethylene (20) sorbitan monolaurate solution, polyethylene glycol sorbitan monolaurate, polyethylene glycol trimethylnonyl ether, and polyethylene glycol p-(1,1,3,3-tetramethylbutyl)-phenyl ether.

In some embodiments, the activated carboxylate group has been reacted with a succinimide, to form a succinimide ester derivative group prior to providing the first solution.

Again, in some embodiments, the chemical moiety which is capable of binding to one or more acid and/or mercury contaminants may be incorporated in the cross-linked polymer network by adding a precursor compound of the chemical moiety to the first polymer solution when the superabsorbent hydrogel is formed through the addition of a cross-linking agent to that solution. Chemical moieties capable of binding with an acid gas are preferably included in the superabsorbent hydrogel in this manner. In other embodiments, the acid gas binding functionality is included in the cross-linked hydrophilic polymer structure of the superabsorbent hydrogel.

In one embodiment, the desired particle size of the superabsorbent hydrogel particles prepared by employing step A is determined by controlling droplet size of the first solution in the second solution. Advantageously, there is no need for size selection after synthesis of the superabsorbent hydrogel particles in the manner described above.

With respect to step B, the desired particle size of the superabsorbent hydrogel particles may be determined by classifying the comminuted freeze-dried cross-linked polymer with one or more suitably sized sieves or other conventional classification techniques as will be understood by those skilled in the art.

It will be appreciated that the above method may further comprise contacting superabsorbent hydrogel particles of a desired particle size prepared according to step A or step B with a liquid phase or an aqueous solution of one or more compounds capable of removing an acid gas and/or mercury contaminant, wherein the superabsorbent hydrogel particles absorb the liquid phase or the aqueous solution within the cross-linked polymer network.

A hygroscopic salt as described previously may be incorporated into the superabsorbent hydrogel particles prepared as described above by contacting the superabsorbent hydrogel particles with an aqueous solution of the hygroscopic salt.

Alternatively, the first solution further comprises the hygroscopic salt.

Method for Removing One or More Contaminants from a Hydrocarbon Gas

The particulate material as described herein is capable of absorbing water and other contaminants, in particular acid gas contaminants, from hydrocarbon gas. Accordingly, the disclosure provides a method for removing one or more acid gas and/or mercury contaminants from a hydrocarbon gas.

The method comprises contacting the hydrocarbon gas with superabsorbent hydrogel particles comprising a cross-linked polymer network having from 0.1 mol % to 50 mol % cross-linking agent, wherein the superabsorbent hydrogel particles incorporate one or more compounds or chemical moieties capable of binding an acid gas and/or mercury contaminant. The superabsorbent hydrogel may be as described herein.

The superabsorbent hydrogel particles may be capable of forming a bed. The bed may be a stationary bed or a moving bed, such as a fluidised bed. Therefore in some embodiments contacting the hydrocarbon gas with the superabsorbent hydrogel particles may comprise passing a stream of hydrocarbon gas through a bed of the superabsorbent hydrogel particles. The bed may reside in a vessel or a column through which the stream of hydrocarbon gas may pass as it undergoes various processing steps. For example, the stationary bed may reside in a dehydration column or an acid gas recovery unit (AGRU). Advantageously, the morphology of the superabsorbent hydrogel particles may be selected to allow the superabsorbent hydrogel particles to swell whilst maintaining flow of the stream of hydrocarbon gas through the interstitial voids between the swollen superabsorbent hydrogel particles.

The superabsorbent hydrogel particles as described herein may also be capable of flowing. Therefore in some embodiments contacting the hydrocarbon gas with the superabsorbent hydrogel particles may comprise introducing a flow of superabsorbent hydrogel particles into a hydrocarbon gas stream. The superabsorbent hydrogel particles may be fluidised in any suitable carrier fluid, such as a gas or a liquid. The flow of superabsorbent hydrogel particles mixes with the hydrocarbon gas stream, thereby absorbing water and, optionally, other contaminants, in particular acid gas contaminants from the hydrocarbon gas stream. Spent superabsorbent hydrogel particles (i.e. contaminant-loaded particulate superabsorbent hydrogel materials) may be separated from the hydrocarbon gas stream downstream in the gas processing plant or gas flowline by conventional separation techniques, such as filtration or centrifugation, after isolating the spent superabsorbent hydrogel particles from the hydrocarbon gas stream in a slug catcher.

The method may further comprise regenerating the separated superabsorbent hydrogel particles prior to subsequently reintroducing the regenerated superabsorbent hydrogel particles upstream into the hydrocarbon gas stream. Any suitable regeneration process as will be well understood by one of skill in the art may be employed.

Separated water-loaded superabsorbent hydrogel particles may be heated to remove water from the cross-linked hydrophilic polymer network of the superabsorbent hydrogel. The separated water-loaded superabsorbent hydrogel particles may be heated by contacting said particles with a hot gas stream derived from elsewhere in the gas processing plant. For example, a bed of said particles may be heated between 200° C. to 315° C. by passing a hot gas stream through the bed. Alternatively, said particles may be thermally regenerated at a lower temperature (e.g. about 75° C.) when a negative pressure is applied to said particles. Advantageously, substantially all absorbed water may be removed from the superabsorbent hydrogel by employing thermal regeneration techniques, such that the regenerated superabsorbent hydrogel particles exhibits reproducible absorptive capacity over a plurality of regeneration cycles.

Alternatively, water-loaded superabsorbent hydrogel particles may be regenerated by de-swelling said superabsorbent hydrogel particles in a water-miscible solvent in which the superabsorbent hydrogel is not soluble. Illustrative examples of such water-miscible solvents include, but are not limited to, ethanol, methanol, THF and so forth.

Separated acid gas-loaded superabsorbent hydrogel particles may undergo any one of several suitable regeneration processes to remove acid gas from the cross-linked hydrophilic polymer network of the superabsorbent hydrogel. Illustrative examples of such regeneration processes to remove acid gas from the acid gas-loaded superabsorbent hydrogel particles include, but are not limited to, pressure swing adsorption, vacuum swing adsorption, temperature swing adsorption, electric swing adsorption, and a hybrid pressure and temperature swing adsorption process. Alternatively, the acid gas-loaded superabsorbent hydrogel particles may be washed in a solvent in which the superabsorbent hydrogel is not soluble but in which solvent the acid gas is soluble.

In some embodiments, a plurality of different regeneration techniques may be used to regenerate the contaminant-loaded superabsorbent hydrogel particles. In these embodiments, a plurality of stationary beds of the contaminant-loaded superabsorbent hydrogel particles may be provided, wherein each stationary bed is configured to undergo a respective regenerative process to remove a specific contaminant.

It will be appreciated that for some contaminants, in particular mercury, it may be more cost effective to dispose the contaminant-loaded superabsorbent hydrogel particles than to regenerate them.

It will also be appreciated that at least a portion of the regenerated particulate superabsorbent hydrogel material may be recycled upstream.

The regenerated particulate superabsorbent hydrogel material may have a higher weight percentage water saturation relative to a weight percentage saturation of the acid gas and/or mercury contaminant. The relative rates of absorption of the acid gas contaminants and water are likely to differ depending on the various characteristics of the superabsorbent hydrogel, including its water content, and the nature and concentration of the one or more compounds or chemical moieties incorporated into the superabsorbent hydrogel. Therefore the performance of the contaminant absorption process may be enhanced through recycling a portion of partially hydrated particulate superabsorbent hydrogel materials. This may be particularly advantageous as the increased water content may also improve absorption of the acid gas contaminant.

In other embodiments, two or more particulate superabsorbent hydrogel materials may be employed, with each particulate superabsorbent hydrogel material arranged to remove a specific contaminant. For example a first particulate superabsorbent hydrogel material may incorporate one or more compounds or chemical moieties capable of binding a first acid gas and/or mercury contaminant. A second particulate superabsorbent hydrogel material may incorporate one or more compounds or chemical moieties capable of binding a second acid gas and/or mercury contaminant.

The first contaminant may be the same or different to the second contaminant. For example, the first contaminant may be carbon dioxide and the second contaminant may be hydrogen sulphide or mercury.

The hydrocarbon gas may be contacted with the first particulate superabsorbent hydrogel material and subsequently contacted with the second particulate superabsorbent hydrogel materials to sequentially remove the first and second contaminants. The first and second particulate superabsorbent hydrogel materials may be provided in a first and second vessel, respectively, wherein the second vessel is located downstream of the first vessel.

Alternatively, a flow of the first particulate superabsorbent hydrogel material may be introduced into a hydrocarbon gas stream upstream of the second particulate superabsorbent hydrogel material. In this arrangement the gas flowline may be provided with respective entry and exit ports to receive and discharge separate flows of the first and second particulate superabsorbent hydrogel materials.

Each exit port may be in fluid communication with a regeneration unit configured to regenerate the first or second contaminant-loaded particulate superabsorbent hydrogel material discharged from the gas flowline. At least a portion of the regenerated materials may be recycled to their respective entry ports.

In one particular embodiment, the first and second particulate superabsorbent hydrogel material may be separable through size, density or other means.

Alternatively, the hydrocarbon gas may be contacted with a mixture of the first and second particulate superabsorbent hydrogel materials to remove the first and second contaminants simultaneously. The relative amounts of said first and second materials in the mixture may be varied depending on the composition of the feed gas and the relative concentration of the first and second contaminants in the feed gas.

The superabsorbent hydrogel particles as described herein provide several advantages in comparison to conventional dehydration media and sweetening methods employed in gas processing plants.

For example, liquid chemical or physical solvents, which are conventionally employed for natural gas sweetening (i.e. removal of acid gases from the hydrocarbon stream), typically undergo regeneration processes involving more than one step, are subject to 'foaming' because of contamination of the solvent, and require a relatively large footprint in a gas processing plant, not only for the AGRU but also for a regeneration unit. Additionally, there may be significant energy consumption associated with operating the regeneration unit.

In contrast, use of the particulate material as described herein for gas sweetening avoids the problem of 'foaming' because the liquid chemical or physical solvent is absorbed and contained within discrete superabsorbent hydrogel particles. Furthermore, regeneration of the spent superabsorbent hydrogel particles may be achieved in a single or reduced number of process steps, resulting in a smaller footprint in the gas processing plant and reduced capital and operating costs.

In comparison to other solid contaminant removal media, such as molecular sieves and absorption membranes, the hydrogel particles as described herein also demonstrate greater absorptive capacity with respect to water and/or other contaminants. Consequently, a smaller volume of superabsorbent hydrogel particles may be employed in the methods described herein in comparison to the solid media counterparts (e.g. molecular sieves, silica gel), further reducing the footprint required for these process steps in the gas processing plant. Additionally, the superabsorbent hydrogel particles are also lighter than their solid media counterparts which is beneficial for transport and storage thereof, particularly on offshore processing facilities.

Furthermore, conventional gas processing plants employ different absorption media and discrete processes to sequentially remove acid gas and water from hydrocarbon gas. Advantageously, the superabsorbent hydrogel particles as described herein are capable of simultaneous removal of water and acid gas from hydrocarbon gas. The ability to combine removal of water and acid gas in a single step with a single material provides significant reduction in capital and operational expenditure as well as reducing the footprint required from gas dehydration and gas sweetening in the gas processing plant.

Some embodiments of said method will now be described with reference to FIGS. 1 and 2, where like reference numerals refer to like features throughout.

Figure 1:
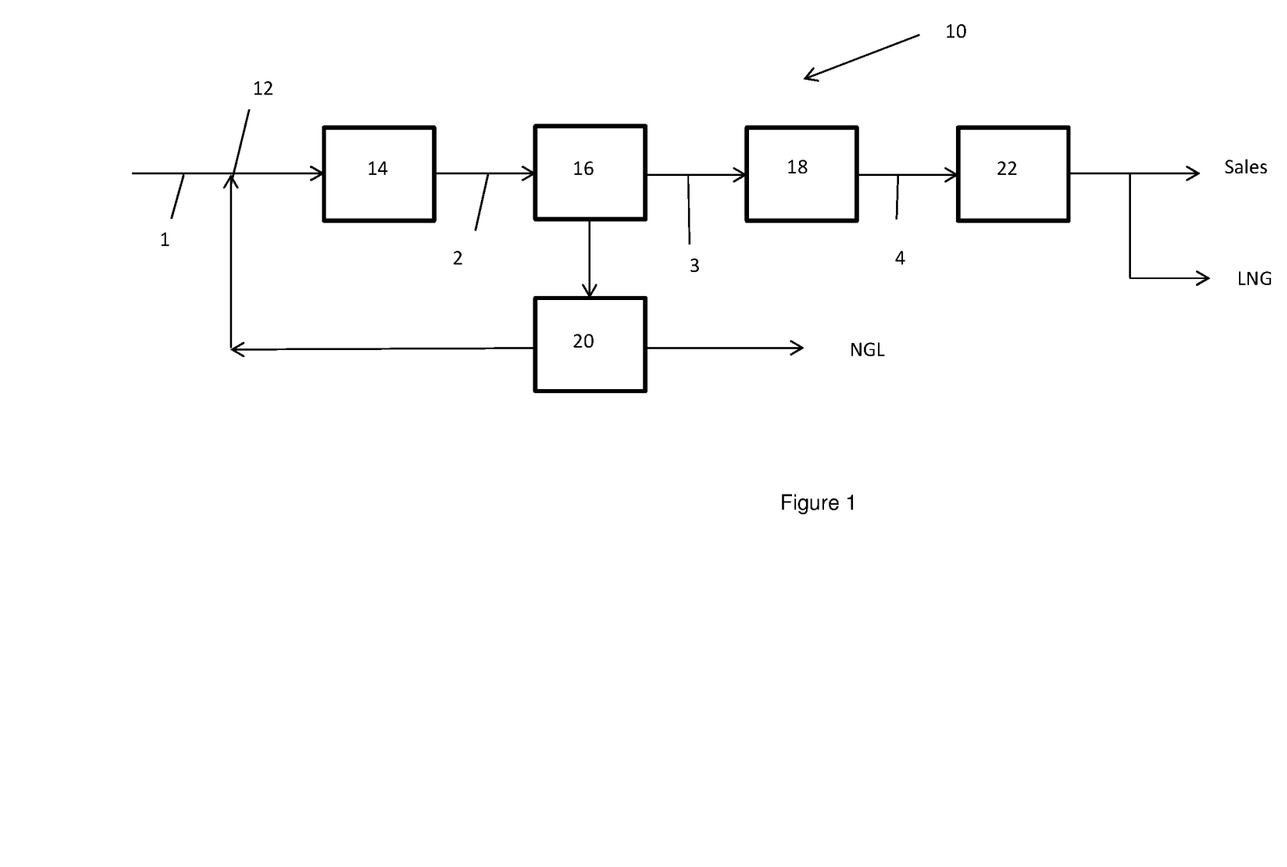
FIG. 1 is a schematic representation of a natural gas processing plant illustrating a first embodiment of the particulate superabsorbent hydrogel material and methods as described herein for the removal of water and sour gas contaminants from a natural gas stream.

Referring to FIG. 1, in accordance with various aspects of the present invention, there is shown a natural gas processing plant 10. In this particular embodiment a feed gas from a wellhead is introduced into the plant via line 1. A flow of superabsorbent hydrogel particles as described herein may be introduced through an input port 12 into line 1 to mix with and/or flow co-currently with the feed gas. The input port 12 may be an input port as configured for injection of monoethylene glycol (MEG) into line 1 for prevention of hydrate formation. In some embodiments, the superabsorbent hydrogel particles may be co-injected with MEG into line 1.

The superabsorbent hydrogel particles will absorb water and/or other contaminants from the feed gas, such as carbon dioxide. The mixture of the feed gas and superabsorbent hydrogel particles may be passed to a heat exchanger 14 where the mixture is cooled to ambient temperature. Depending on the composition of the feed gas, bulk water and heavy hydrocarbon condensates may condense in the heat exchanger 14. The cooled feed gas is passed via line 2 to a separator 16 (or a slug catcher) to separate any condensed liquids and contaminant-loaded hydrogel particles therefrom. The condensed liquids are separated from the contaminant-loaded superabsorbent hydrogel particles and directed elsewhere in the plant 10 for further processing. The separated cooled feed gas is passed via line 3 to an AGRU 18.

The contaminant-loaded superabsorbent hydrogel particles collected in the separator 16 (or slug catcher) may be directed to a regeneration plant 20 and subsequently returned to the input port 12 for re-introduction into the line 1.

The AGRU 18 may be provided with a stationary bed of superabsorbent hydrogel particles as described herein. The separated cooled feed gas is passed through the stationary bed in the AGRU 18 for removal of one or more acid gas contaminants therefrom.

Depending on the residual water content of the resulting sweetened gas, the sweetened gas may optionally be passed to a dehydration unit 22 via line 4. The dehydration unit 22 may comprise a column packed with superabsorbent hydrogel particles as described herein. Passing the sweetened gas through the column in the dehydration unit 22 removes the residual water content and the resulting dehydrated gas may be compressed and transported as sales gas through a distribution pipeline. Alternatively, the resulting dehydrated gas may be passed to a LNG train for liquefaction as LNG.

Figure 2:
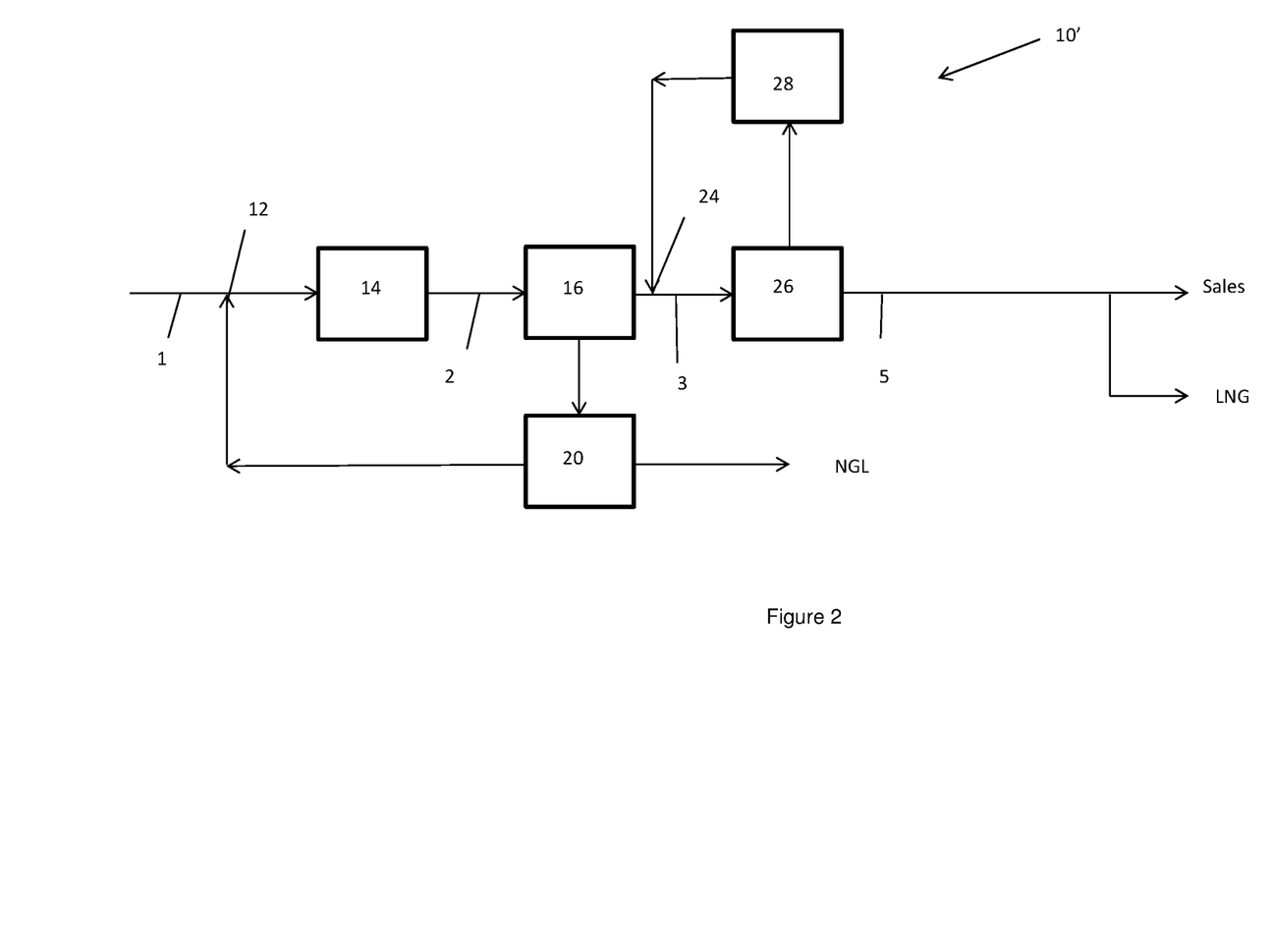
FIG. 2 is a schematic representation of a natural gas processing plant illustrating a second embodiment of the particulate superabsorbent hydrogel material and methods as described herein for the removal of water and sour gas contaminants from a natural gas stream; and, FIG. 3 is a graphical representation of the comparative respective water absorptive capacities of molecular sieves (MS), triethyl glycol TEG, a first absorbent in accordance with one embodiment of the disclosure, the first absorbent after undergoing regeneration; and a second absorbent in accordance with another embodiment of the disclosure.
Figure 3:
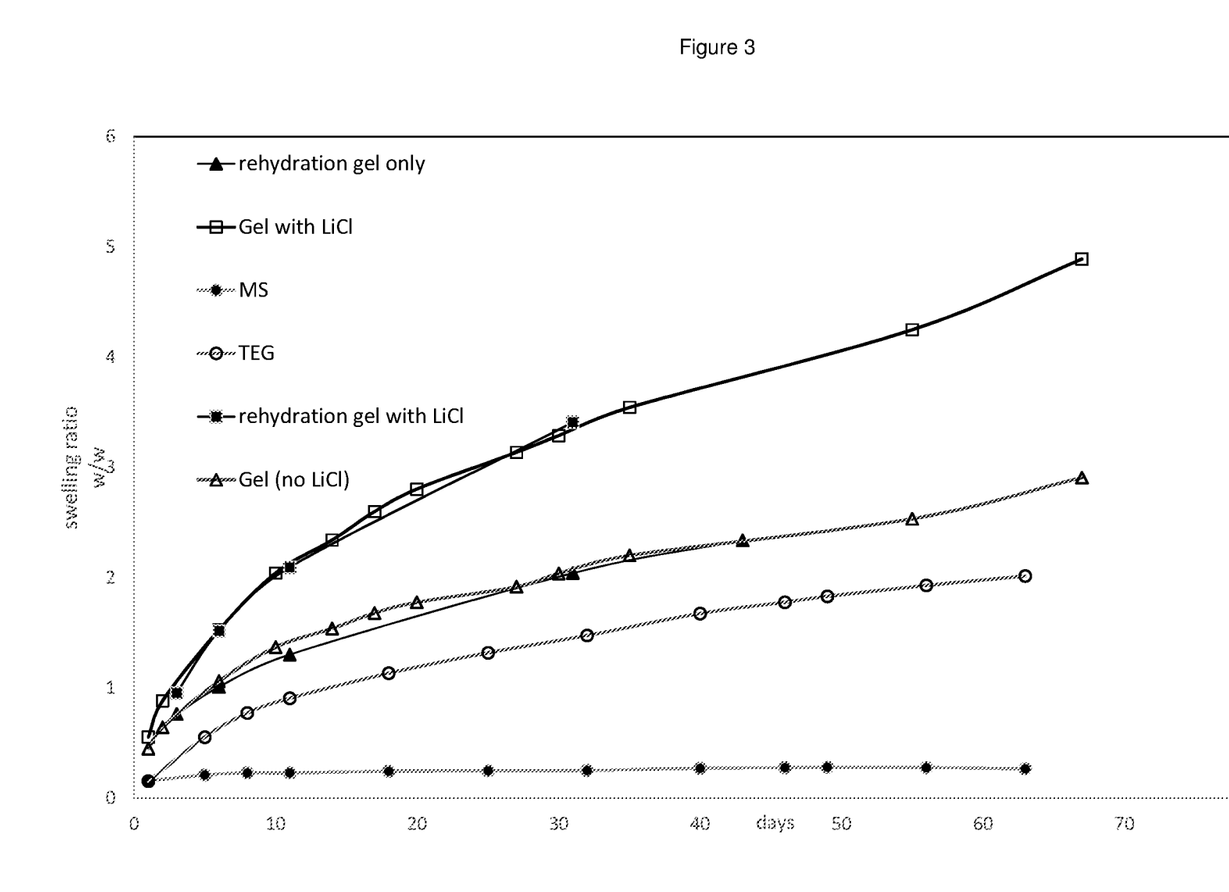

Referring to FIG. 2, in accordance with various aspects of the present invention, there is shown a natural gas processing plant 10'. In this particular embodiment a feed gas from a wellhead is introduced into the plant via line 1. A flow of first particulate superabsorbent hydrogel material as described herein may be introduced through an input port 12 into line 1 to mix with and/or flow co-currently with the feed gas. The input port 12 may be an input port as configured for injection of monoethylene glycol (MEG) into line 1 for prevention of hydrate formation. In some embodiments, said first material may be co-injected with MEG into line 1.

The first particulate superabsorbent hydrogel material absorbs water and carbon dioxide. The mixture of the feed gas and first particulate superabsorbent hydrogel material may be passed to a heat exchanger 14 where the mixture is cooled to ambient temperature. Depending on the composition of the feed gas, bulk water and heavy hydrocarbon condensates may condense in the heat exchanger 14. The cooled feed gas is passed via line 2 to a separator 16 (or a slug catcher) to separate any condensed liquids and contaminant-loaded superabsorbent hydrogel particles therefrom. The condensed liquids are separated from the contaminant-loaded first particulate superabsorbent hydrogel material and directed elsewhere in the plant 10 for further processing.

The contaminant-loaded first particulate superabsorbent hydrogel material is collected in the separator 16 (or slug catcher), directed to a regeneration plant 20 and subsequently returned to the input port 12 for re-introduction into the line 1.

A flow of second particulate superabsorbent hydrogel material for absorbing a second contaminant, such as hydrogen sulphide, is introduced upstream of separator 16 through input port 24 in line 3. The flow of second particulate material mixes with the partially sweetened gas separated in separator 16 in line 3 and further sweetens the partially sweetened gas by removing hydrogen sulphide therefrom.

The mixture may be directed to slug catcher 26 which separates contaminant-loaded second particulate material from the sweetened gas. The sweetened gas is directed through line 5 to be compressed and transported as sales gas through a distribution pipeline. Alternatively, the resulting sweetened gas may be passed to a LNG train for liquefaction as LNG. The contaminant-loaded superabsorbent hydrogel particles collected in the slug catcher 26 may be directed to a regeneration plant 28 and subsequently returned to the input port 24 for re-introduction into the line 3.

As described above with reference to FIG. 2, it may be desirable to employ more than one particulate superabsorbent hydrogel material for removal of different contaminants for the purpose of optimising mass transfer with two or more contaminants being removed at different rates.

Method for Dehydrating a Hydrocarbon Gas

The particulate material as described herein is capable of absorbing free water, thereby dehydrating a hydrocarbon gas. Accordingly, the disclosure provides a method for dehydrating a hydrocarbon gas.

The method comprises contacting a hydrocarbon gas with particulate superabsorbent hydrogel material comprising a cross-linked hydrophilic polymer network having from 0.1 mol % to 50 mol % cross-linking agent, wherein said polymer network optionally incorporates one or more compounds or chemical moieties capable of binding water. The particulate superabsorbent hydrogel material may be as described herein.

Method for Mitigating Hydrate Formation in Gas Flowlines

Depending on the temperature and pressure conditions, there is a risk of formation of solid methane hydrates in gas flowlines if the water content of the hydrocarbon gas is sufficiently high. The particulate material as described herein is capable of absorbing free water, thereby preventing agglomeration and deposition of methane hydrates in flowlines for transport of hydrocarbon gas. Accordingly, the disclosure provides a method for mitigating hydrate formation in gas flowlines.

The method comprises introducing into a gas flowline a plurality of superabsorbent hydrogel particles comprising a cross-linked hydrophilic polymer network having from 0.1 mol % to 50 mol % cross-linking agent, wherein the superabsorbent hydrogel particles optionally incorporate one or more compounds or chemical moieties capable of binding an acid gas and/or mercury contaminant. The particulate superabsorbent hydrogel material may be as described herein.

Method for Mitigating Corrosion

The particulate material as described herein may be capable of absorbing acid gases in addition to free water, thereby reducing potential for corrosion in a flowlines for transport of hydrocarbon gas and/or processing equipment. Accordingly, in a further aspect of the disclosure there is provided a method for mitigating corrosion in a gas processing plant and/or gas flowlines.

The method comprises introducing into a gas processing plant and/or a gas flowline a plurality of superabsorbent hydrogel particles comprising a cross-linked polymer network having from 0.1 mol % to 50 mol % cross-linking agent, wherein the superabsorbent hydrogel particles incorporate one or more compounds or chemical moieties capable of binding an acid gas and/or mercury contaminant.

EXAMPLE

The invention is further illustrated by the following example. The example is provided for illustrative purposes only. It is not to be construed as limiting the scope or content of the invention in any way.

Example 1. Synthesis of Superabsorbent Hydrogel

Superabsorbent hydrogel microspheres were generated in an inverse suspension. EDC (0.3993 g) was dissolved in 0.5 mL of distilled water and added to 5 mL of an aqueous solution of PAM-co-AA (15 w/v %) and the resulting highly viscous solution was mixed. After 3 mins, 0.24 g of NHS dissolved in 0.5 mL of distilled water was added, at this stage the viscosity of the solution decreased. This activated polymer solution was then added drop-wise over a five minute period to 95 mL of heptane containing 5 w/v % Span 60 in a 250 mL round bottom flask heated to 50° C. The solution was continuously stirred at 1000 rpm using a magnetic stir bar (32×16 mm egg shaped) to provoke droplet generation. This mixture was termed an inverse suspension of activated polymer and consisted of an aqueous polymer phase suspended as droplets in heptane. After five minutes the cross-linking agent (0.063 g EDA), dissolved in 0.5 mL of water, was added drop-wise to the inverse suspension which initiates the reaction. The reaction was complete after only 40 minutes at 50° C. and the resulting superabsorbent hydrogel microspheres were isolated by filtering through a filter funnel that was heated to 60° C. Alternatively, the microspheres were added to excess ethanol (500 mL) and were then filtered.

Example 2. Alternative Synthesis of Hydrogel

An alternative to inverse suspension polymerization is to freeze dry superabsorbent hydrogel blocks. The freeze dried resulting porous network can be ground and sieved to form particles. In this case the superabsorbent hydrogel was attached to a freeze dryer in separated glass vials. Total dry and foamed polymers were generated in the glass vials after about 4 hrs in the vacuum condition. These polymers were removed from the vials and ground using mortar and pestle. To assist grinding, dry ice was applied to enhance the brittleness as needed. Fine particles of roughly similar size were generated.

Example 3. Hydration of Superabsorbent Hydrogel Particles

The dry superabsorbent hydrogel particles were placed in a glass jar, and sufficient heptane was added to cover the particles with a magnetic stirrer in the jar. Water was added in a dropwise manner while stirring vigorously, whilst ensuring the particles were separated in the jar. Water addition ended when all the particles became transparent. At this stage, the weight ratio of water and particles was approximately 3:1. The heptane was decanted and the gel jar was left open in a fume hood for 3 hrs until the heptane is vaporized completely. At this stage a cluster of bead-like gel were formed.

Example 4. Incorporation of an Acid Gas Removal Fluid

The partially swollen superabsorbent hydrogel particles containing water were dried by precipitating the polymer in ethanol to remove the water. The resulting dried polymer was swollen in a 20% w/w monoethanolamine solution.

Example 5. Comparative Examples with Respect to Water Absorption

The absorptive capacities for water of several particulate materials including molecular sieves (MS) having a 3 Å pore diameter, triethylene glycol (TEG), a first absorbent comprising a superabsorbent hydrogel formed by crosslinking 15% PAM-co AA with EDA with LiCl inclusion (2.5 M) and a second absorbent comprising a superabsorbent hydrogel formed by crosslinking 15% PAM-co AA with EDA without LiCl inclusion were measured gravimetrically. The results are compared in FIG. 1.

The first absorbent and molecular sieves were then regenerated in a vacuum oven at 75° C. for 15 h. The first absorbent reached its original weight, 100% dry, while the molecular sieves achieved 90% dryness, indicating that the regeneration process is more efficient for absorbents of the embodiments described herein.

The absorptive capacity for water of the regenerated first absorbent was then also measured gravimetrically (FIG. 1). The absorptive capacity for water of the regenerated first absorbent is similar to the first absorbent, indicating that the first absorbent may be re-used after regeneration without significant deterioration in absorptive capacity.

The first absorbent absorbed 15-17 times more water than MS and 2.2-2.4 times more than TEG. The second absorbent absorbed 9-11 times more water than MS and 25-50% more water than TEG.

Example 6

The partially swollen superabsorbent hydrogel particles described in Example 4 were gravimetrically tested for uptake of carbon dioxide by allowing the superabsorbent hydrogel particles to reside in a desiccator filled with dry ice for a period of time. The superabsorbent hydrogel particles increased in weight by 52% after approximately 8 h.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A self-supporting flowable particulate material having an average particle size of from about 10 pm to about 2000 nm for removing an acid gas and/or mercury contaminant from a hydrocarbon gas comprising a superabsorbent hydrogel comprising a cross-linked hydrophilic polymer network having from 0.1 mol % to 50 mol % cross-linking agent, wherein the superabsorbent hydrogel incorporates one or more compounds capable of binding the acid gas and/or mercury contaminant, wherein said one or more compounds are absorbed into the superabsorbent hydrogel as a liquid phase or an aqueous solution thereof, and wherein said one or more compounds comprises an acid gas absorbent selected from the group consisting of an alkanolamine, alkylamine, alkyloxyamines, piperidine and its derivatives, piperazine and its derivatives, pyridine and its derivatives, polyethylene glycol-dimethyl ethers (Selexol), N- methylpyrrolidone, propylene carbonate, methanol, sulfolane, imidazoles, ionic liquids, primary amines, secondary amines, tertiary amines, sterically hindered amines, mixtures of one or more of the preceding liquids, alkali or alkaline earth metal carbonate solutions, alkali or alkaline earth metal hydroxide solutions, and alkali or alkaline earth metal phosphate solutions.

2. The particulate material according to claim 1, further comprising a hygroscopic salt incorporated into the cross-linked hydrophilic polymer network.

3. The particulate material according to claim 2, wherein the hygroscopic salt comprises lithium chloride, lithium bromide, calcium chloride or calcium sulphate.

4. The particulate material according to claim 1, wherein the superabsorbent hydrogel comprises a functionalised crosslinked polymer comprising PAM-co-AA that has been crosslinked with EDC, NHS and multifunctional amines.

5. The particulate material according to claim 1, wherein the superabsorbent hydrogel in a partially dehydrated state comprises:
  a) 0.05 to 5 wt % cross-linked hydrophilic polymer;
  b) 0.5 to 60 wt % water; and
  c) 99 to 40 wt % of one or more compounds capable of binding a contaminant other than water.

6. The particulate material according to claim 1, wherein the acid gas absorbent is selected from the group consisting of monoethanolamine, diethanolamine, methyldiethanolamine, diisopropanolamine, and/or aminoethyoxyethanol.

7. The particulate material according to claim 1, wherein a final modulus of the cross-linked hydrophilic polymer network is from 0.1 Pa to 12000 Pa.

8. The particulate material according to claim 1, wherein the hydrogel incorporates one or more chemical moieties capable of binding the acid gas and/or mercury contaminant.

9. The particulate material according to claim 8, wherein incorporation of the one or more chemical moieties into the superabsorbent hydrogel comprises covalently bonding the one or more chemical moieties to the cross-linked hydrophilic polymer network.

10. The particulate material according to claim 9, wherein the one or more chemical moieties is derived from:
  a monomer having one or more functional groups capable of binding to, or reacting with, the acid gas and/or mercury contaminant, wherein the monomer is copolymerized or crosslinked to the cross-linked hydrophilic polymer network; a group grafted onto the cross-linked hydrophilic polymer network having one or more functional groups capable of binding to, or reacting with, the acid gas and/or mercury contaminant; and/or
  a cross-linking agent having one or more functional groups capable of binding to, or reacting with, the acid gas and/or mercury contaminant, wherein the cross-linking agent is crosslinked with a hydrophilic polymer to form the cross-linked hydrophilic polymer network.

11. A method of preparing a self-supporting flowable particulate material gas according to claim 1 comprising:
  (i) providing a first solution comprising:
    (a) hydrophilic polymer having a repeating monomer unit comprising at least two different pendant functional groups;
    (b) a cross-linking agent having at least two pendant functional groups capable of forming a covalent bond with the hydrophilic polymer;
  wherein at least one of the at least two pendant functional groups of the repeating monomer unit or the cross-linking agent is capable of binding to or reacting with an acid gas and/or mercury contaminant; and wherein at least one of the at least two pendant functional groups of the repeating monomer is a carboxyl or activated carboxylate group and the cross-linking agent is capable of forming a covalent bond with the carboxyl or activated carboxylate group;
  (ii) reacting the cross-linking agent with the polymer so that superabsorbent hydrogel particles comprising a cross-linked polymer having 0.1 mol % to 50 mol % cross-linked polymer network are formed,
  wherein a desired particle size is formed by either:
    (A) suspending the first solution within a second solution, wherein the first solution is immiscible with the second solution, then subsequently reacting the cross-linking agent with the polymer; or
    (B) freeze drying the cross-linked polymer; and then comminuting the freeze dried cross-linked polymer to form dried superabsorbent hydrogel particles of a desired size; and
  (iii) contacting said superabsorbent hydrogel particles with a liquid or an aqueous solution of one or more compounds capable of removing an acid gas and/or a mercury contaminant, whereby said superabsorbent hydrogel particles absorb the liquid phase or the aqueous solution within the cross-linked polymer network.

12. The method according to claim 11, wherein the desired particle size of the superabsorbent hydrogel particles in process A is determined by controlling droplet size of the first solution in the second solution.

13. The method according to claim 11, the method further comprising the step of adding a functionalised agent, the functionalised agent containing at least one pendant functional group capable of forming a covalent bond with a carboxyl or activated carboxylate group on the cross-linked polymer.

14. The method according to claim 11, wherein a weight percentage of the one or more compounds in the superabsorbent hydrogel particles is controlled by:
  a) varying the concentration of the one or more compounds in the aqueous solution, or b) varying a period of time the superabsorbent hydrogel particles contact the liquid phase or the aqueous solution.

15. The method according to claim 11, wherein step (iii) comprises contacting the superabsorbent hydrogel particles with a first liquid or a first aqueous solution of a first compound capable of removing a first acid gas and/or mercury contaminant to produce a partially swelled hydrogel having the first liquid or aqueous solution absorbed therein and subsequently contacting said partially swelled hydrogel with a second liquid or a second aqueous solution of a second compound capable of removing a second acid gas and/or mercury contaminant.

16. The method according to claim 11, the method further comprising step (iv) drying the superabsorbent hydrogel particles produced in step (iii).

17. A method for removing one or more acid gas and/or mercury contaminants from a hydrocarbon gas comprising contacting a hydrocarbon gas with self-supporting flowable particulate superabsorbent hydrogel material according to claim 1.

18. The method according to claim 17, wherein acid gas and/or mercury contaminant-loaded particulate superabsorbent hydrogel material undergoes one or more regeneration processes.

19. The method according to claim 18, wherein at least a portion of the regenerated particulate superabsorbent hydrogel material is recycled upstream.

20. The method according to claim 18, wherein the regenerated particulate superabsorbent hydrogel material has a higher weight percentage water saturation relative to a weight percentage saturation of the acid gas and/or mercury contaminant.

21. The method according to claim 17, wherein removing one or more acid gas and/or mercury contaminants from a hydrocarbon gas comprises contacting the hydrocarbon gas with a first particulate superabsorbent hydrogel material and a second particulate superabsorbent hydrogel material.

22. The method according to claim 21, wherein the first particulate superabsorbent hydrogel material incorporates one or more compounds or chemical moieties capable of binding a first acid gas and/or mercury contaminant and the second particulate hydrogel material incorporates one or more compounds or chemical moieties capable of binding a second acid gas and/or mercury contaminant different from said first contaminant.

23. The method according to claim 22, wherein hydrocarbon gas is contacted with a mixture of the first and second particulate superabsorbent hydrogel materials or the hydrogen gas is contacted with the first particulate superabsorbent hydrogel material and subsequently contacted with the second particulate hydrogel materials to sequentially remove said first and second contaminants.

24. The method of claim 17, wherein contacting the hydrocarbon gas with the particulate superabsorbent hydrogel material comprises introducing a flow of particulate superabsorbent hydrogel material into the hydrocarbon gas stream.

25. The method of claim 17, wherein contacting the hydrocarbon gas with the particulate superabsorbent hydrogel material comprises passing a stream of the hydrocarbon gas through a bed of the particulate superabsorbent hydrogel material.

* * * * *

UNITED STATES PATENT AND TRADEMARK OFFICE
CERTIFICATE OF CORRECTION

| | |
|---|---|
| PATENT NO. | : 11,325,102 B2 |
| APPLICATION NO. | : 16/463457 |
| DATED | : May 10, 2022 |
| INVENTOR(S) | : Colin Wood |

It is certified that error appears in the above-identified patent and that said Letters Patent is hereby corrected as shown below:

In the Claims

At Column 25, Lines 12-34, Claim 1 should read:
-- 1. A self-supporting flowable particulate material having an average particle size of from about 10 μm to about 2000 μm for removing an acid gas and/or mercury contaminant from a hydrocarbon gas comprising a superabsorbent hydrogel comprising a cross-linked hydrophilic polymer network having from 0.1 mol% to 50 mol% cross-linking agent, wherein the superabsorbent hydrogel incorporates one or more compounds capable of binding the acid gas and/or mercury contaminant, wherein said one or more compounds are absorbed into the superabsorbent hydrogel as a liquid phase or an aqueous solution thereof, and wherein said one or more compounds comprises an acid gas absorbent selected from the group consisting of an alkanolamine, alkylamine, alkyloxyamines, piperidine and its derivatives, piperazine and its derivatives, pyridine and its derivatives, polyethylene glycol-dimethyl ethers (Selexol), N-methylpyrrolidone, propylene carbonate, methanol, sulfolane, imidazoles, ionic liquids, primary amines, secondary amines, tertiary amines, sterically hindered amines, and mixtures of one or more of the preceding liquids, alkali or alkaline earth metal carbonate solutions, alkali or alkaline earth metal hydroxide solutions, or alkali or alkaline earth metal phosphate solutions. --

Signed and Sealed this
Second Day of May, 2023

Katherine Kelly Vidal
*Director of the United States Patent and Trademark Office*